United States Patent
Silva et al.

(10) Patent No.: US 10,258,402 B2
(45) Date of Patent: Apr. 16, 2019

(54) ORTHOPEDIC BONE PLATE SYSTEM

(71) Applicant: OsteoCertus, LLC, Pembroke Pines, FL (US)

(72) Inventors: Cesar Silva, Pembroke Pines, FL (US); David Augusto Silva, Popayán (CO)

(73) Assignee: OsteoCertus, LLC, Pembroke Pines, FL (US)

( * ) Notice: Subject to any disclaimer, the term of this patent is extended or adjusted under 35 U.S.C. 154(b) by 435 days.

(21) Appl. No.: 14/987,425

(22) Filed: Jan. 4, 2016

(65) Prior Publication Data

US 2017/0189086 A1    Jul. 6, 2017

(51) Int. Cl.
| A61B 17/80 | (2006.01) |
| A61B 17/88 | (2006.01) |
| A61B 17/86 | (2006.01) |
| A61B 90/00 | (2016.01) |

(52) U.S. Cl.
CPC ...... *A61B 17/8863* (2013.01); *A61B 17/8052* (2013.01); *A61B 17/8057* (2013.01); *A61B 17/8085* (2013.01); *A61B 17/8605* (2013.01); *A61B 2090/037* (2016.02)

(58) Field of Classification Search
CPC ... A61B 17/80; A61B 17/8085; A61B 17/808; A61B 17/8023; A61B 17/8057; A61B 17/86

See application file for complete search history.

(56) References Cited

U.S. PATENT DOCUMENTS

| 5,002,544 A | 3/1991 | Klaue et al. |
| 5,053,036 A | 10/1991 | Perren et al. |
| 5,151,103 A | 9/1992 | Tepic et al. |
| 5,564,302 A | 10/1996 | Watrous |
| 5,690,631 A | 11/1997 | Duncan et al. |
| 6,001,099 A | 12/1999 | Huebner |
| 6,309,393 B1 | 10/2001 | Tepic et al. |
| 6,348,052 B1 | 2/2002 | Sammarco |
| 6,454,770 B1 | 9/2002 | Klaue |

(Continued)

FOREIGN PATENT DOCUMENTS

| KR | 101201603 B1 | 10/2011 |
| WO | WO2014/074850 A1 | 5/2014 |

OTHER PUBLICATIONS 1.5 mm LCP Modular Mini Fragment System. 1.5 mm instrument and implant modules. Technique Guide, Synthes, 2009.

(Continued)

*Primary Examiner* — Christopher Beccia
(74) *Attorney, Agent, or Firm* — Gordon & Jacobson, P.C.

(57) ABSTRACT

A bone plate is asymmetric and includes a straight body and a cross arm. The plate has first and second sides, each with the same structure. The body and cross arm include nodes separated by deformable bridges. Each node defines a screw hole, and wings extending laterally therefrom. The wings taper in thickness between the first and second sides. Screw holes are threaded into the nodes. Each of the first and second sides of the body and cross arm define longitudinal channels in the nodes. The plate can be shaped to the bone by deformation at the bridges or removal of portions of the plate at bridges. A pair of benders, each with clamp bracket and clamping bolt threadedly coupled within a threaded hole of the bracket, is also provided for shaping the plate.

32 Claims, 13 Drawing Sheets

(56) References Cited

U.S. PATENT DOCUMENTS

| | | |
|---|---|---|
| 6,004,353 A1 | 12/2006 | Masini |
| 7,189,237 B2 | 3/2007 | Huebner |
| 7,704,251 B2 | 4/2010 | Huebner et al. |
| 7,740,634 B2 | 6/2010 | Orbay et al. |
| 7,771,433 B2 | 8/2010 | Orbay et al. |
| 7,935,126 B2 | 5/2011 | Orbay et al. |
| 8,080,010 B2 | 12/2011 | Schulz et al. |
| 8,167,918 B2 | 5/2012 | Strnad et al. |
| 8,172,886 B2 | 5/2012 | Castaneda et al. |
| 8,231,663 B2 | 7/2012 | Kay et al. |
| 8,292,898 B2 | 10/2012 | Castaneda et al. |
| 8,419,745 B2 | 4/2013 | Sixto, Jr. et al. |
| 8,518,088 B2 | 8/2013 | Castaneda et al. |
| 8,568,462 B2 | 10/2013 | Sixto, Jr. et al. |
| 8,632,574 B2 | 1/2014 | Kortenbach et al. |
| 8,702,763 B2 | 4/2014 | Lin et al. |
| 8,992,582 B1 | 3/2015 | Knoepfle et al. |
| 2004/0092935 A1 | 5/2004 | Manderson |
| 2004/0097936 A1 | 5/2004 | Ebid |
| 2005/0149026 A1 | 7/2005 | Butler et al. |
| 2006/0004362 A1 | 1/2006 | Patterson et al. |
| 2008/0015591 A1 | 1/2008 | Castaneda et al. |
| 2008/0221574 A1 | 9/2008 | Cavallazzi et al. |
| 2009/0281543 A1 | 11/2009 | Orbay et al. |
| 2009/0299369 A1 | 12/2009 | Orbay et al. |
| 2010/0069966 A1* | 3/2010 | Castaneda ......... A61B 17/1728 606/280 |
| 2010/0131012 A1* | 5/2010 | Ralph ................ A61B 17/80 606/280 |
| 2011/0022049 A1 | 1/2011 | Huebner et al. |
| 2011/0092981 A1 | 4/2011 | Ng et al. |
| 2011/0144698 A1 | 6/2011 | Buchbinder et al. |
| 2012/0065689 A1 | 3/2012 | Prasad et al. |
| 2012/0109214 A1 | 5/2012 | Leither et al. |
| 2013/0023938 A1 | 1/2013 | Huebner et al. |
| 2013/0204307 A1 | 8/2013 | Castaneda et al. |
| 2014/0000092 A1 | 1/2014 | Fritzinger et al. |

OTHER PUBLICATIONS

Graduated Stability Plates (GSP), Stryker, Leibinger Micro Implant Products, 2004.

Product Rationale & Surgical Technique, ALPS Total Foot System, Biomet Orthopedics, 2012.

* cited by examiner

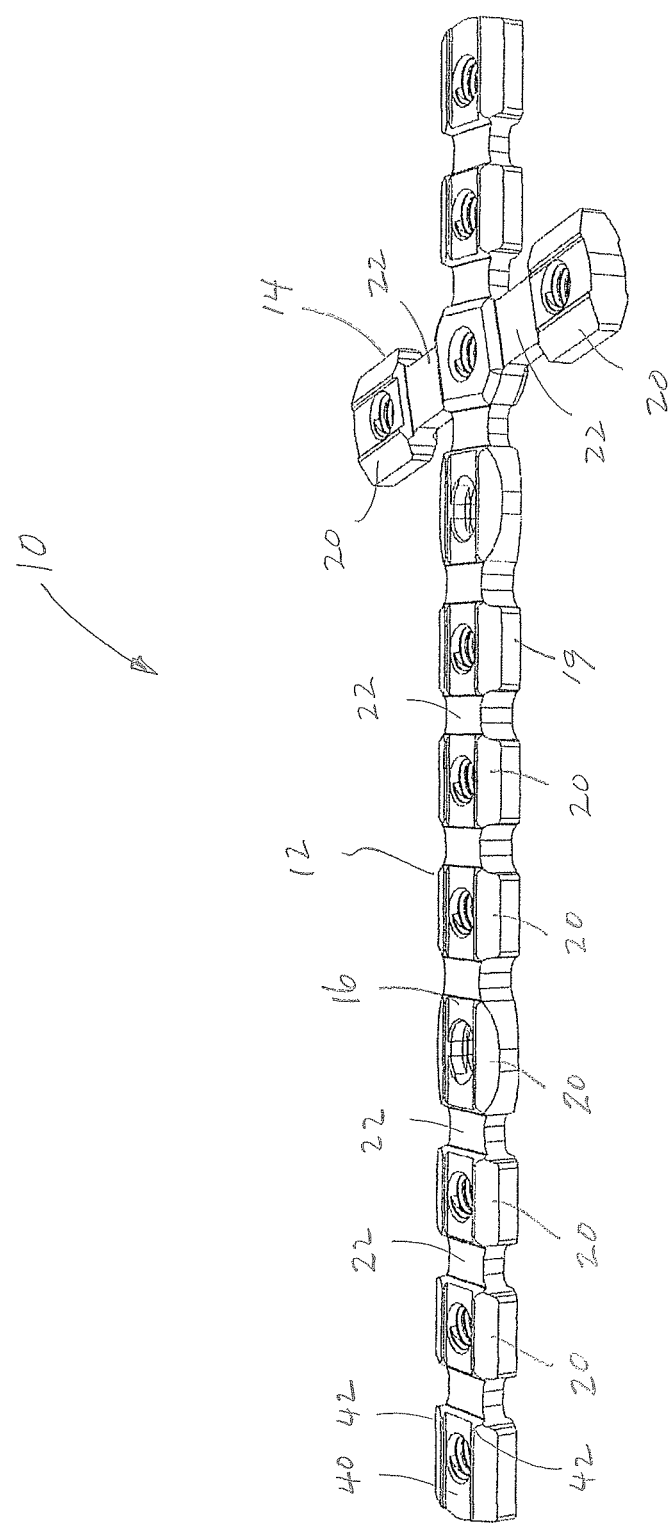

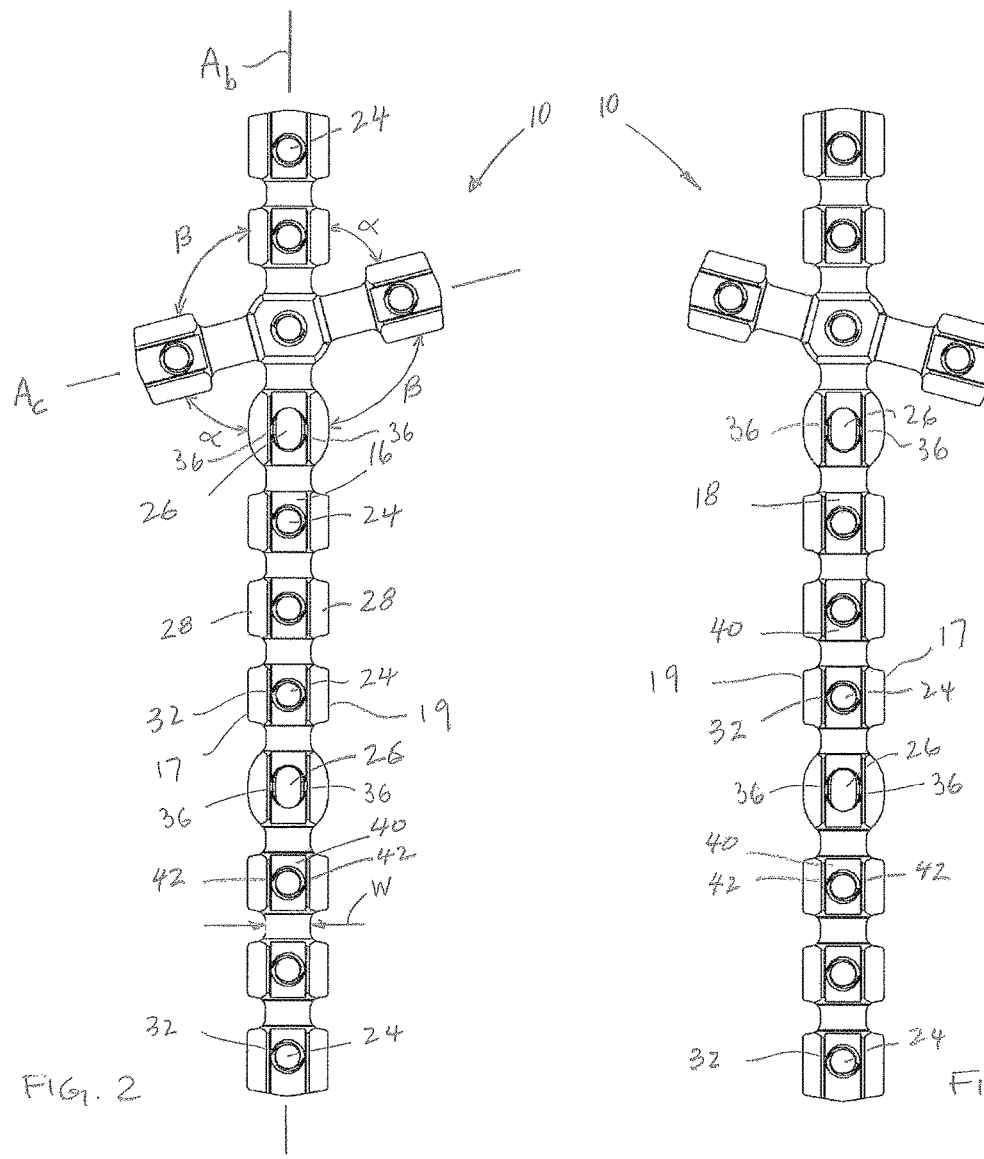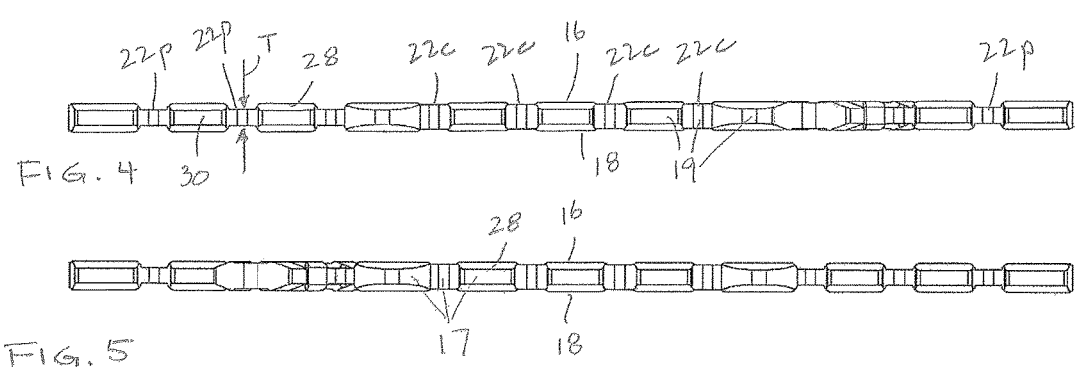

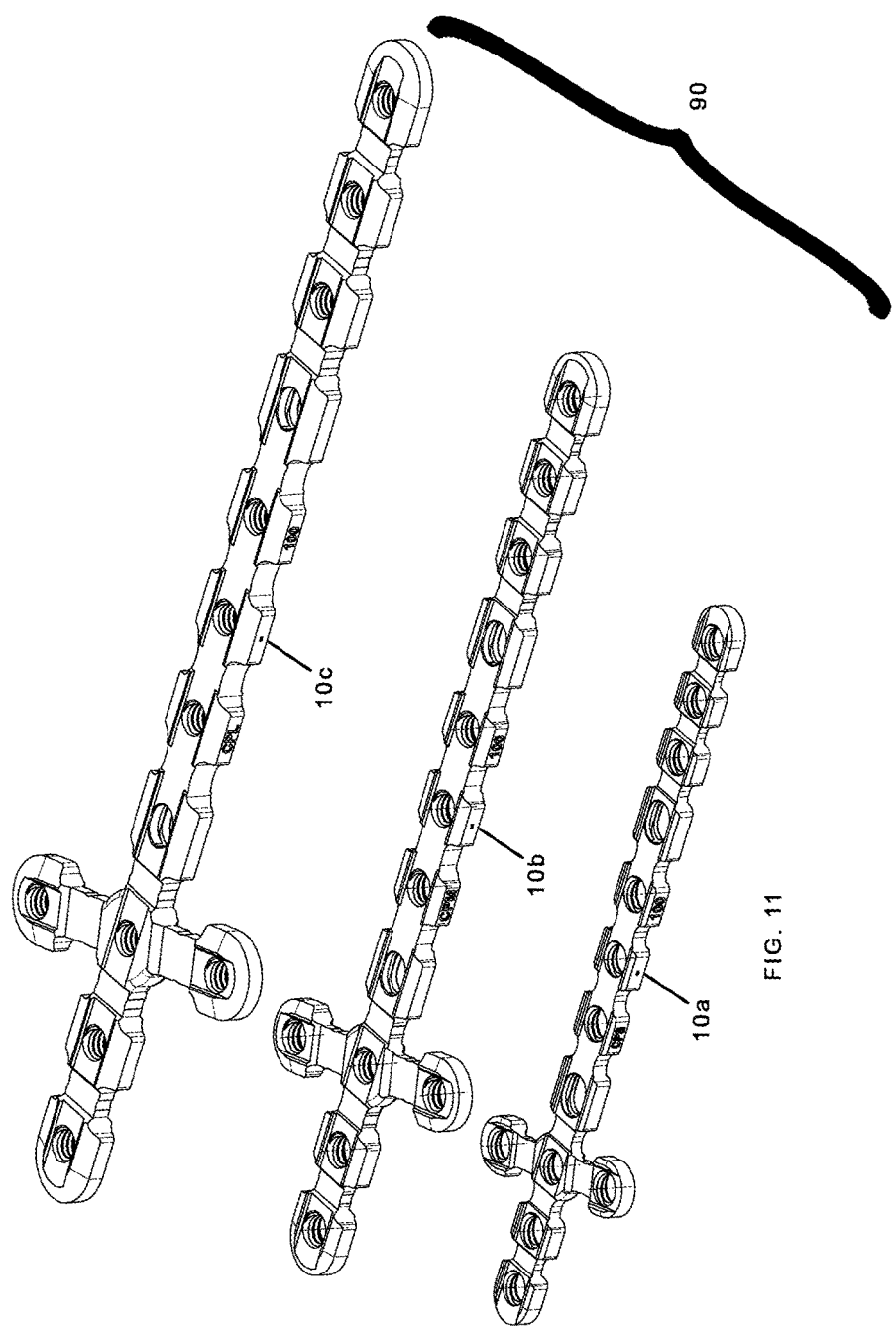

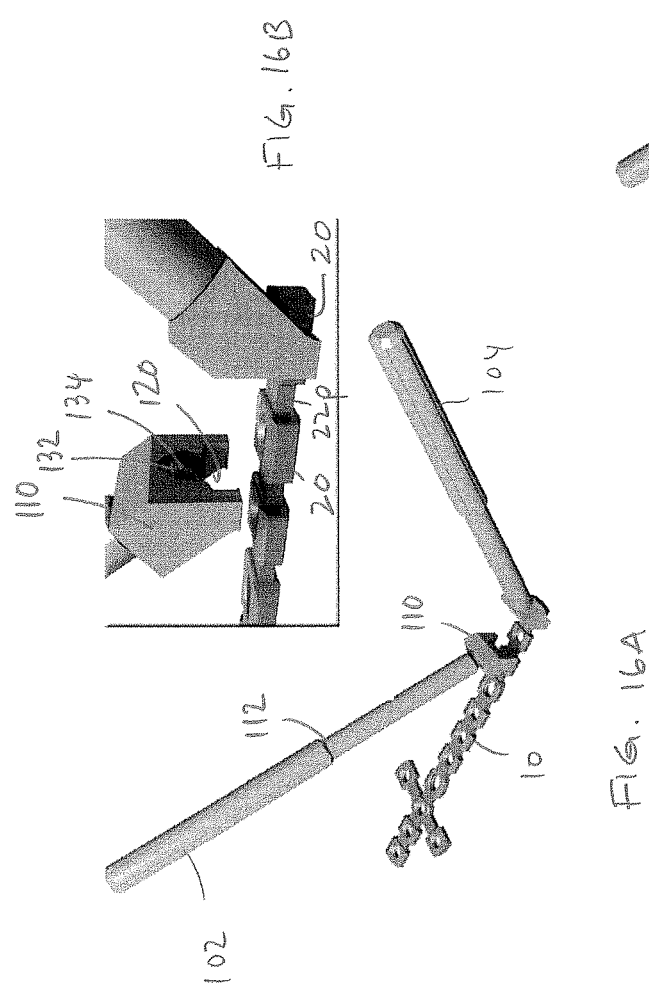

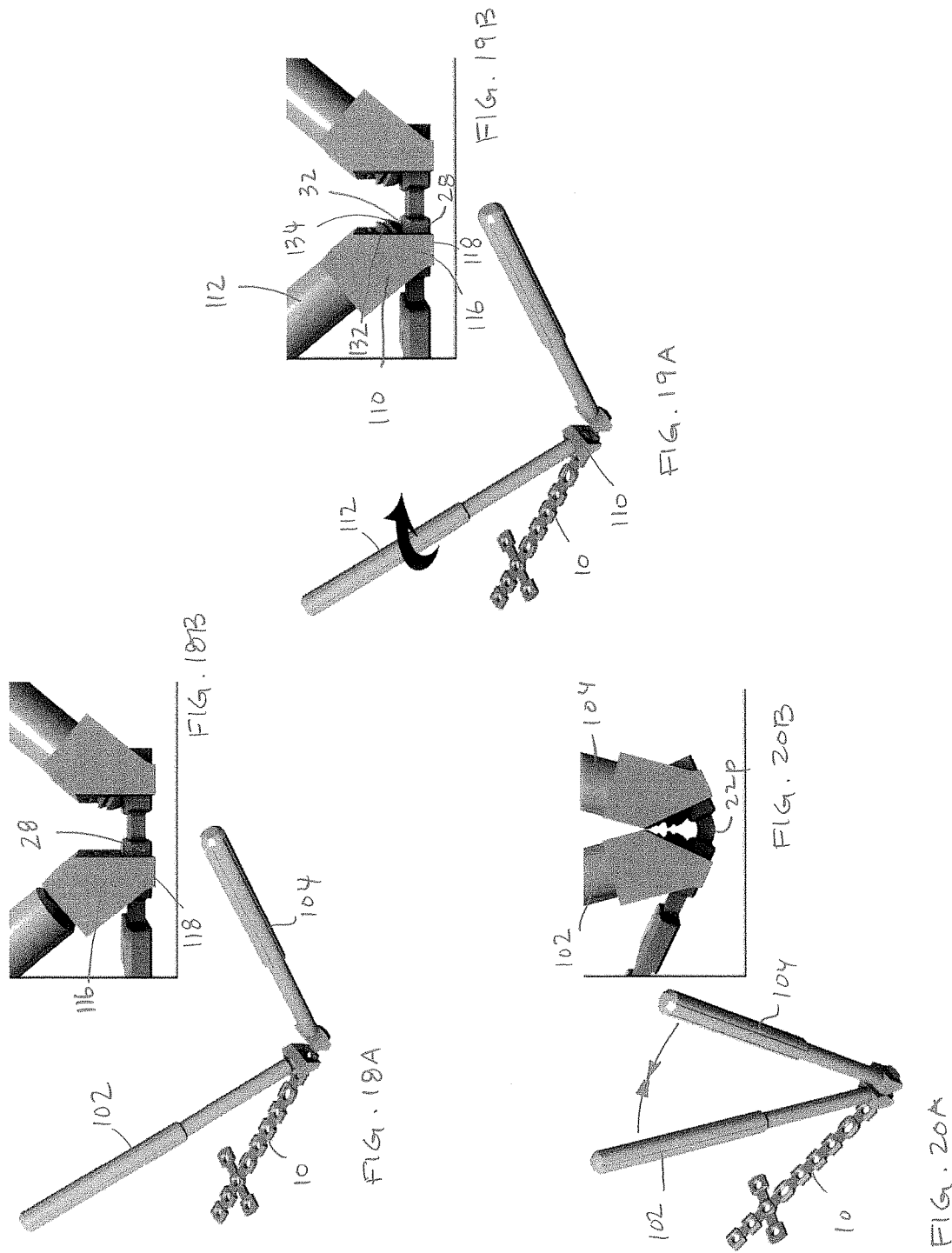

ORTHOPEDIC BONE PLATE SYSTEM

BACKGROUND

1. Field

The present invention relates to surgery. More particularly, the invention relates to bone plates for internal orthopedic fixation in mammals.

2. State of the Art

Orthopedic plates are known for treating traumatic bone injuries in humans and other mammals. With respect to human treatment, significant development has been made in designing plates that are less of a general elongate form, but rather are more particularly adapted to the specific bones for which they are intended. That is, there has been a trend toward developing anatomical plates. In an anatomical plate, the bone-contacting surface of the plate closely fits the surface contours of the bone to which the plate is specifically adapted. These plates are generally provided in two versions of mirrored symmetry for use on the bones of the left and right sides of the body.

While good results have been reported with such anatomical plates, their use requires that treatment centers maintain a large inventory of different plates, each adapted for the different bones of the body, bones of different sizes, and the left and right sides of the body. The maintenance of such an extensive inventory can be costly, which is a significant disadvantage for treatment centers that may use certain plates with only a low frequency.

Further, while for a human population, the expense of a costly inventory often can be justified or required, animal populations do not benefit from such luxury. Veterinary surgical plates are often more basic than their human counterparts, of a general purpose, and not well adapted to the anatomical contours of the bone.

SUMMARY

A limited set of bone plates, each of like design but of a different size, are provided that can be adapted for treatment of many different types of bone fractures and bone sizes. According to one aspect of each bone plate, each plate is planar, in the form of a 't', and, in an embodiment, consists of a straight body and a cross arm. According to another aspect of the bone plate, the cross arm extends transverse to the body at a non-orthogonal angle. The bone plate has a first side and a second side. According to another aspect of the bone plate, each of the first and second sides are adapted with same structure and contours such that each can be positioned against and in contact with the bone being treated, thereby providing treatment for bones on one lateral side of the body when the first side is positioned against the bone, and treatment for bones on the other lateral side of the body when the second side is positioned against a respective bone. As such, the plates have the same structure at their first and second sides.

More particularly, the body and cross arm of each plate include nodes separated by deformable bridges. The body portion defines a body axis extending centrally along the bridges of the body. The cross arm includes a cross axis extending centrally along the bridges of the cross arm. Each node defines a central screw hole, and wings extending laterally outward from the axis on which the node is situated. The wings taper in thickness between the first and second sides. The screw holes in a plurality of the nodes are preferably threaded, and in at least one node is preferably an elongate slot. The threaded screw holes all include an upper countersink.

The body and cross arm further define respective central longitudinal channels on each of the first and second sides of the plate in which the screw holes of the nodes are positioned. The channels have sides defining a pair of rails. When the first side of the plate is placed into contact with the bone, the rails seat against the bone and allow a convex bone extend into the channels, and the channels at the second side define respective spaces in which screw heads of screws within the screw holes may be recessed. Similarly, when the second side of the plate is placed into contact with the bone, the rails on the second side seat against the bone, and the channels at the first side define respective spaces in which screw heads of screws within the screw holes may be recessed. The nodes at a more central location of the plate are stiffer and more resistant to deformation.

The plate may be shaped by removal of portions of the plate at bridges between the nodes. The removal can be performed with a cutting instrument or by reverse bending until breakage at a selected bridge. The plate may be further shaped to the bone by plastic deformation of the plate at the bridges between the nodes.

In accord with another aspect of the system, a bending system is provided to bend the plates at the bridges between the nodes. The bending system includes first and second benders, each of preferably like structure and assembly. Each bender includes a clamp bracket and a handle. The bracket includes a body, an upper threaded hole in the body, and a pair of spaced-apart arms descending from the body, each terminating in a inwardly directed seat. The space between the seats at the lower ends of the arms is sufficient to be received vertically over a bridge of the plate but too small to accommodate vertical passage over the wings of a node. However, the space between the arms in relation to the wings allows the arms to be moved along the axis from a bridge to an adjacent node, with the lower end of the wings of the node engaging the seats. The handle includes a proximal shaft and a distal threaded clamping bolt which is threadedly coupled within the threaded hole of the bracket and extends into the space between the arms. The end of the clamping bolt is convex and sized to seat against the countersink of a threaded screw hole.

In use, an appropriately sized plate is selected for a bone, such as a long bone or the pelvis. The orientation of the plate is selected, such that one of the first and second surfaces is identified for placement against the bone. The plate is then reshaped as necessary and secured to the bone. The plate may be fully or partially reshaped before any attachment to the bone, or may be preliminarily attached to the bone and then reshaped and further secured.

More particularly, to reshape the plate at a bridge, a pair of benders are positioned on the plate at the two nodes on opposite sides of the bridge. Each bender is placed over a bridge and then slid into place on its respective node. Then the handle is rotated relative to the bracket to cause the clamping bolt to advance against the upper surface of the plate, at the countersink and without entering the threads of the screw hole. When the handle is rotated, the bracket is stably retained on the plate by the position of the arms about the wings of the node. The handle is rotated until the plate is clamped between the clamping bolt and the seats on the arms. Once each bender is coupled to its respective node, a relative force is applied between the benders to deform the bridge and thereby shape the plate.

The system also includes screws for securing the plate to the bone. In a preferred system, both locking screws and compression screws are provided. In addition, screws of different diameter and length are also provided for appropriate fixation and repair of the bone injury.

The system provides a single plate design that accommodates left and right anatomies and which can also be customized in shape via removal of one or more nodes and bending along one or more bridges. The single plate design is readily adaptable into treatment even for those surgeons who have not had significant prior experience with anatomical or shapeable plates adapted for specific bones.

BRIEF DESCRIPTION OF THE DRAWINGS

FIG. 1 is a perspective view of a plate according to a system described herein.

FIG. 2 is a plan view of a first side of the plate of FIG. 1.

FIG. 3 is a plan view of a second side of the plate of FIG. 1.

FIG. 4 is an elevation view from the right side of the plate as oriented in FIG. 2.

FIG. 5 is an elevation view from the left side of the plate as oriented in FIG. 2.

FIG. 11 is a perspective view of a set of plates.

FIG. 16A through 20B illustrate a method of using the system, with the 'A' figures showing the system in total, and the 'B' figures showing enlargements of respective portions in the 'A' figures.

DETAILED DESCRIPTION OF THE PREFERRED EMBODIMENTS

Figure 6:
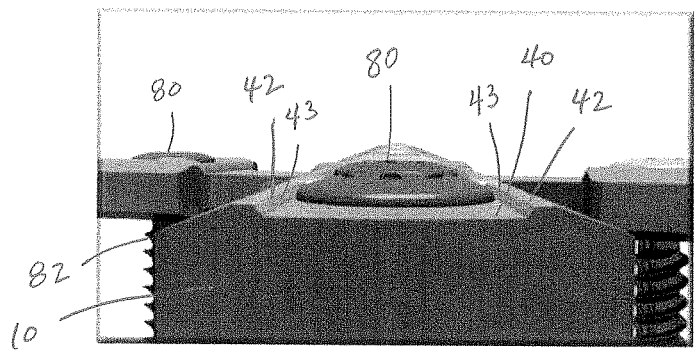
FIG. 6 is a cross sectional perspective view across a body portion of the plate, orthogonal to the longitudinal axis of the body portion.

Turning now to FIGS. 1 through 5, a bone plate 10 is shown. The plate is preferably made of metal, and has sufficient rigidity to provide stability to a broken bone. The bone plate 10 is in the form of a 't' and includes, and in embodiments consists of, a straight body 12 and a straight cross arm 14. The cross arm 14 extends transverse to the body 12 at a non-orthogonal angle, preferably forming two a angles of 75±10°, and two respectively supplementary angles β of 105°±10°, giving the plate a bilaterally asymmetric design.

The bone plate 10 extends in a plane, and has a first side 16, a second side 18, and lateral sides 17, 19 extending between the first and second sides. According to another aspect of the bone plate, each of the first and second sides 16, 18 are adapted with the same structure and contours such that each can be positioned against and in contact with the bone being treated, thereby providing treatment for bones on one lateral side of the body when the first side is oriented as a bone contacting surface, and treatment for bones on the other lateral side of the body when the second side is positioned against a respective bone.

More particularly, each of the body 12 and cross arm 14 of the plate includes a linear arrangement of alternating nodes 20 and bridges 22. The body 12 defines a body axis $A_b$ extending centrally along the bridges 22 of the body. The cross arm 14 includes a cross axis $A_c$ extending centrally along the bridges 22 of the cross arm 14. The bridges 22 have a width W extends orthogonal to the respective axis $A_b$, $A_c$ along which it lies, and a thickness T extending between the first and second sides 16, 18. The bridges 22 have a reduced area moment of inertia relative to the nodes 20 such that the bridges have an increased propensity to bending deformation relative to the nodes when a bending force is applied thereto. Also, the bridges have reduced polar moment of inertia relative to the nodes 20 such that the bridges have an increased propensity to twisting deformation relative to the nodes when a torqueing force is applied thereto.

Each node 20 defines a central screw hole 24 or 26, and wings 28 extending laterally outward from the axis on which the node is situated. The wings 28 taper at a common first angle in thickness equally between the first and second sides 16, 18 such that the lateral ends 30 of the wings are thinner than the thickness of the node and are elevated relative to whichever of the first and second sides 16, 18 is the bone contacting surface of the plate. The screw holes 24, which are provided in a plurality of the nodes, are threaded and include countersinks 32 opening at each of the first and second sides 16, 18; i.e., at each of their ends. The screw holes 26 in two of the relatively longitudinally central nodes of the body 12 are elongate, preferably non-threaded, and define elongate slots. Elongate screw holes 26 include a pair of ledges 36 extending along the sides of the hole that are adapted to functionally either (i) be engaged by the threads on the threaded head of a locking screw and allow locking relative thereto, or (ii) act as a stop for the head of a compression screw. These features are described further below.

The body 12 and cross arm 14 further define respective central longitudinal channels 40 on each of the first and second sides 16, 18 of the plate in which the screw holes 24, 26 of the nodes 20 are positioned. The channels 40 have sides defining a pair of rails 42. When the first side 16 of the plate is made a bone-contacting side, the rails 42 of the first side seat against the bone and allow a convex bone portion to extend at least partially into the channel 40 thereat, and the opposing channel on the second side 18 defines respective spaces on the nodes in which screw heads 80 of screws 82 (FIG. 6) positioned within the screw holes 24 may be recessed. Similarly, when the second side 18 of the plate is placed is made the bone-contacting side and placed into contact with the bone, the rails on the second side seat against the bone, and the channel at the first side defines respective space in which screw heads of screws within the screw holes of the nodes may be recessed. The rails 42 have a beveled medial side 43 extending at an angle.

The bridges 22, at a more central location of the plate; i.e., located between the nodes provided with the elongate screw slots 26, are thicker, stiffer and more resistant to deformation, whereas the relatively proximal, distal, and lateral (more peripheral) bridges $22_p$ are thinner and more susceptible to deformation (FIG. 4). The plate 10 may be shaped to the bone by plastic deformation of the plate at the bridges 22 between the nodes 20. More particularly, the thinner bridges $22_p$ are utilized for shaping, as described in more detail below.

Figure 10:
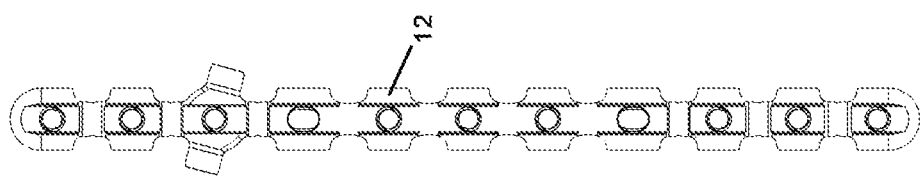
FIGS. 7 through 10 illustrate, in plan view, various exemplar shapes for a plate as shown in FIG. 1, with peripheral portions thereof removed.
Figure 9:
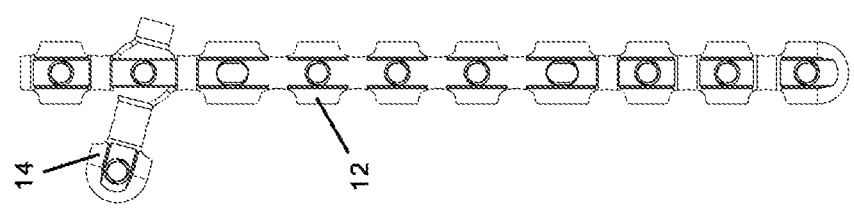
Figure 8:
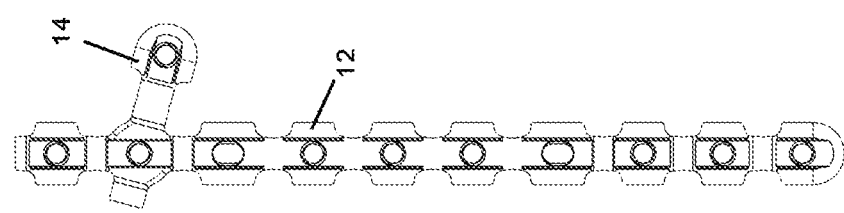
Figure 7:
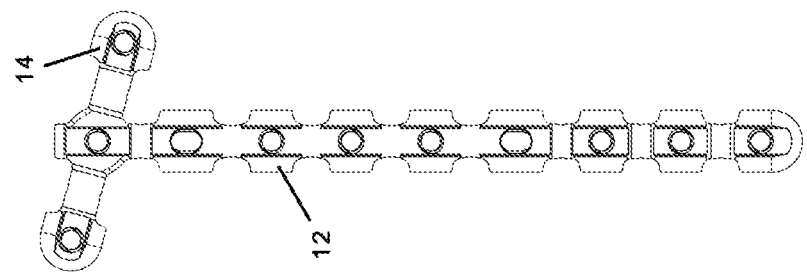

The plate may be further shaped by removal of peripheral portions of the plate at bridges 22 between the nodes. The removal can be performed with a suitable cutting instrument or by reverse bending until breakage at a selected bridge. FIGS. 7 through 10 show various exemplar plate shapes that can be formed by removal of peripheral portions of the plate, preferably about the intersection of the body 12 and cross arm 14. By way of example, the plate can be shaped into a slanted-'T' (FIG. 7), various one-armed shapes (FIGS. 8 and 9), and a straight plate (FIG. 10).

Referring to FIG. 11, in accord with another aspect of the system, a limited set 90 of bone plates, each of like design but of a different size, are provided that can be adapted for treatment of many different types of bone fractures and bone sizes. The set preferably includes exactly three plates, generally a relatively small size plate 10a, a relatively medium size plate 10b, and a relatively large size plate 10c, each for appropriate applications. A fewer or greater number of plates can be provided in the set 90, particularly depending on the population for which the plates are intended and their range of sizes. Such applications may be related to different size bones in the body of a patient, or bones in different patients of different sizes. While the plate can be used in a human population, the plates are particularly adapted for veterinary use, where the animals requiring treatment have a significant range in size between, e.g., small cats to large dogs. By way of example, the small plate is sized to accommodate mammals of 5-15 kg, the medium plate sized to accommodate mammals of 15-25 kg, and the large plate sized to accommodate 25-40 kg, though usage of the plates on mammals of various sizes other than those indicated by example is certainly anticipated.

Figure 12:
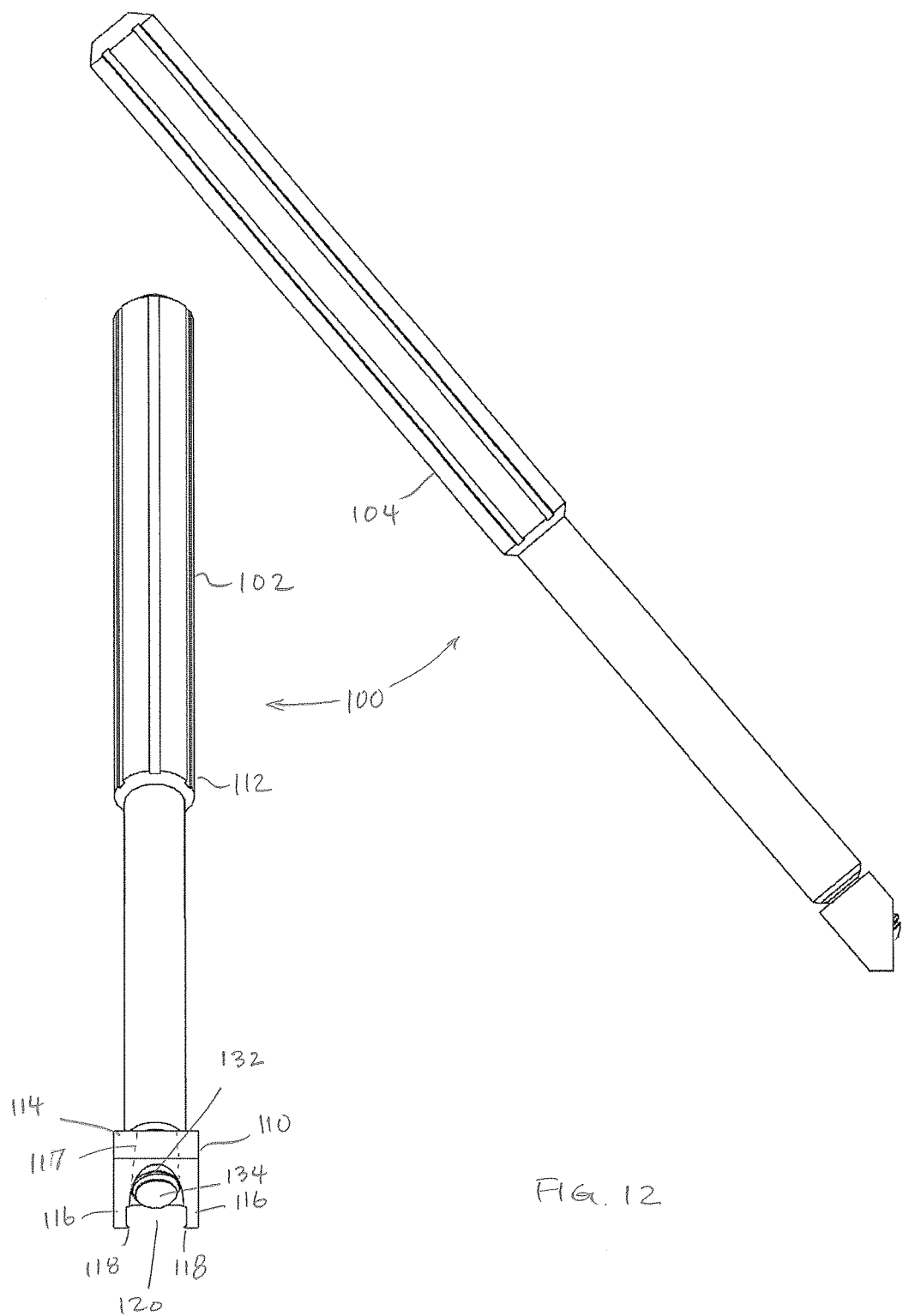
FIG. 12 shows a pair of plate benders, one in front view and one in side elevation view.
Figure 13:
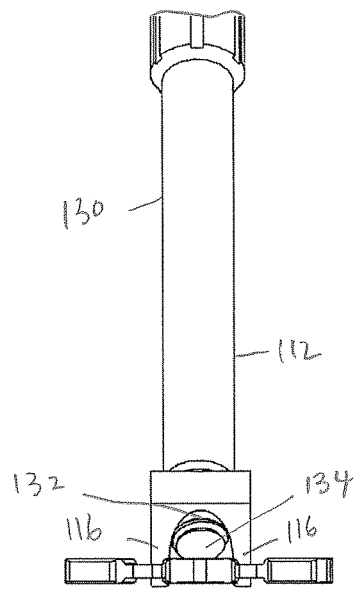
FIG. 13 shows, in a front view, a system of a plate bender coupled to a plate.
Figure 14:
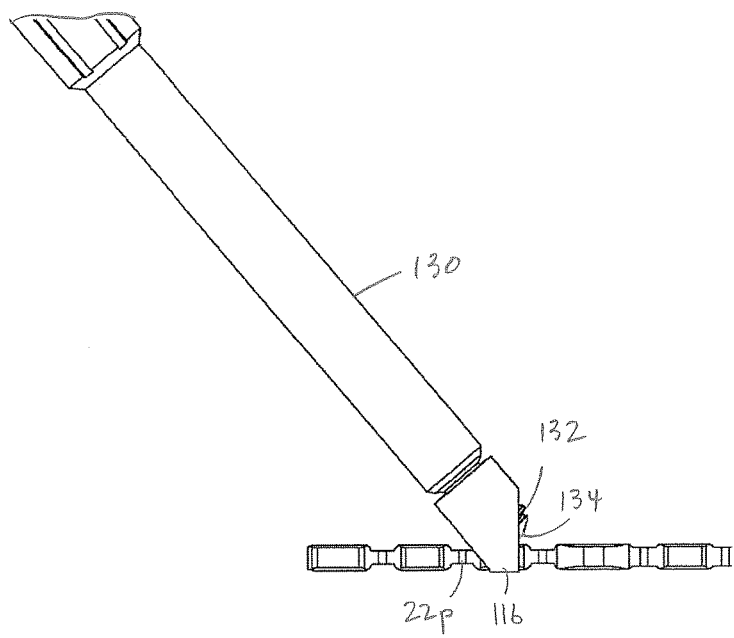
FIG. 14 shows, in a side elevation view, the system of FIG. 13.
Figure 15:
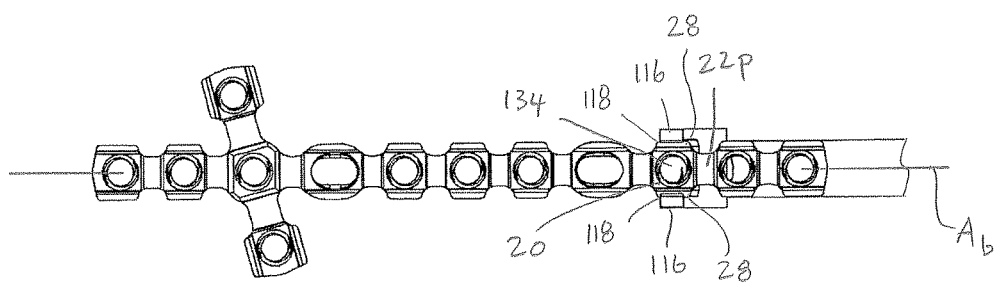
FIG. 15 shows, in a bottom view, the system of FIG. 13.

Turning now to FIG. 12, in accord with another aspect of the system, a bending system 100 is provided to bend the plate 10 at a preferably thinner bridge $20_p$ between two nodes 22. The bending system 100 includes first and second benders 102, 104, each of preferably like structure and assembly. With respect to bender 102, the benders each include a clamp bracket 110 and a handle 112. The bracket 110 includes a body 114, an upper threaded hole 117 defined in the body 114, and a pair of spaced-apart arms 116 descending from the body, which each terminate in an inwardly directed seat 118. A space 120 is defined between the seats 118 at the lower ends of the arms 116. Referring to FIGS. 13 through 15, the space 120 is sufficient to be received vertically over a bridge 22p of the plate but too small to accommodate vertical passage over the wings 28 of an adjacent node. However, the space 120 between the arms and above the seats 118 is sized to allow the arms to be moved along an axis, e.g., $A_b$ from a bridge 22p to an adjacent node 20. The handle 112 includes a proximal shaft 130 rotatably fixed to a distal threaded clamping bolt 132, which is threadedly coupled within the upper threaded hole 117 of the bracket 110 and can be advanced toward (or away from) the seats 118 by rotation (or counter-rotation) of the handle 112 relative to the bracket 110. The end 134 of the clamping bolt 132 is convex and sized to seat against the countersink 32 of a threaded screw hole 24. In a closed clamping position, the handle 112 preferably extends at a transverse angle relative to an axis of the threaded screw hole 24, but may alternatively extend at a 90° angle.

In use, an appropriate sized plate 10 is selected for a bone, such as a long bone or the pelvis. The orientation of the plate is selected such that one of the first and second sides 16, 18 is identified for placement against the bone. The plate is then reshaped, as necessary, and secured to the bone. The plate may be fully or partially reshaped before any attachment to the bone, or may be preliminarily attached to the bone, e.g., via a compression screw at a elongate slot 26, or one or more locking screws at screw holes 24, and then reshaped to accommodate the anatomical contours of the bone. The plate is then further secured with compression screws or fixed angle screws at the threaded holes 24.

More particularly, to reshape the plate 10 at, for example, a bridge 22p, the pair of benders 102, 104 are positioned on the plate at two nodes 20 on opposite sides of the bridge 22p of plate 10. (FIGS. 16A and 16B) (It is appreciated that bridges 22c can also be bent, though they are more rigid than bridges 22p.) If necessary, for each bender, the handle 112 is counter-rotated relative to the bracket 110 to partially withdraw the end 134 of the clamping bolt 132 from the space 120 until sufficient clearance is provided within the space for accommodating the thickness of the node 20. Each bender 102, 104 is placed over a bridge (FIGS. 17A and 17B) and then longitudinally slid into place onto its respective node 20 (FIGS. 18A and 18B). The seats 118 at the ends of the arms 116 are able to grab under the wings 28 (elevated off the bone due to their taper), even when the plate 10 is seated on bone. Then the handle is rotated relative to the bracket to advance the end 134 of the clamping bolt 132 against the upper surface (e.g., first side 116) of the plate at the countersink 32. It is appreciated that when the handle 112 is rotated, the bracket 110 is stably maintained in position on the plate by the engagement of the arms 116 about the wings 28 of the node. The handle 112 is rotated until the plate is clamped between the end 134 of the clamping bolt 132 and the seats 118 on the arms. The bolt 132 is sized to seat on the countersink 32 and not enter the threaded screw hole 24 (FIG. 3). Thus, the end 134 of the bolt cannot deform the threads of the screw hole 24. When the bolt 132 is tightened against the plate 10, the end 134 of the bolt on one side of the plate and the seats 118 at the opposite side of the plate provide three points of contact against the plate for stably gripping the plate. Once each bender 102, 104 is stably coupled to its respective node, a relative force is applied between the benders to deform the bridge $22_p$ therebetween and thereby shape the plate 10 (FIGS. 20A and 20B).

While bending of the plate has been described using a pair of plate benders 102, 104, the plate may also be bent using a single plate bender of the type described in conjunction with an alternate secondary plate stabilizer or bender. By way of example, the alternate secondary bender may comprise a shaft that couples relative to a node coaxial with a threaded screw hole. The shaft may threadedly engage the screw hole 24 to apply force to the node or maintain position of the node. Such an alternate bender may be preferred in circumstances where access to the bone does not readily permit use of the angled-shaft benders.

Figure 21:
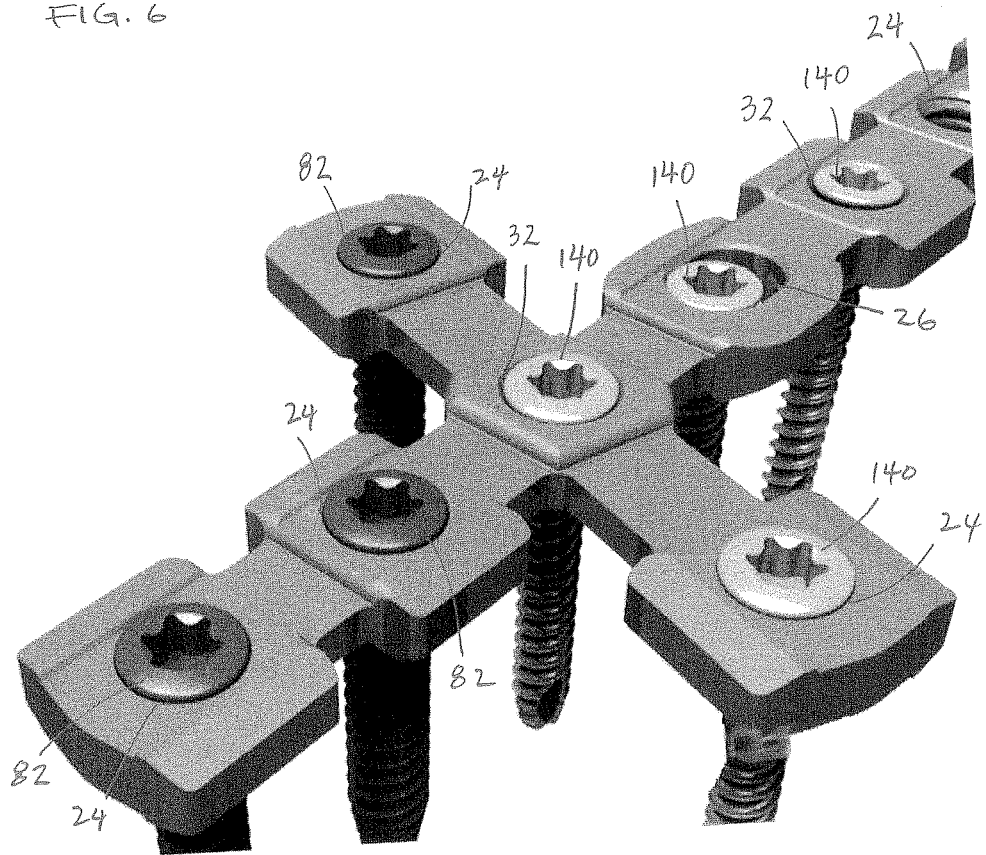
FIG. 21 is a broken perspective view of the system of a plate provided with screws.

As shown in FIGS. 6 and 21, the system also includes screws for securing the plate to the bone. In a preferred system, both locking screws 82 and compression screws 140 are provided. In addition, screws of different diameter and length are also provided for appropriate fixation and repair of the bone injury. The threaded screw holes 24 are adapted to receive both of the locking screws 82 and compression screws 140. The locking screws 82 threadedly engage with the threaded screw holes 24. The compression screws 142 having a lower head surface that engages the countersink 32 above the threads of screw holes 24.

Figures 22A, 22B:
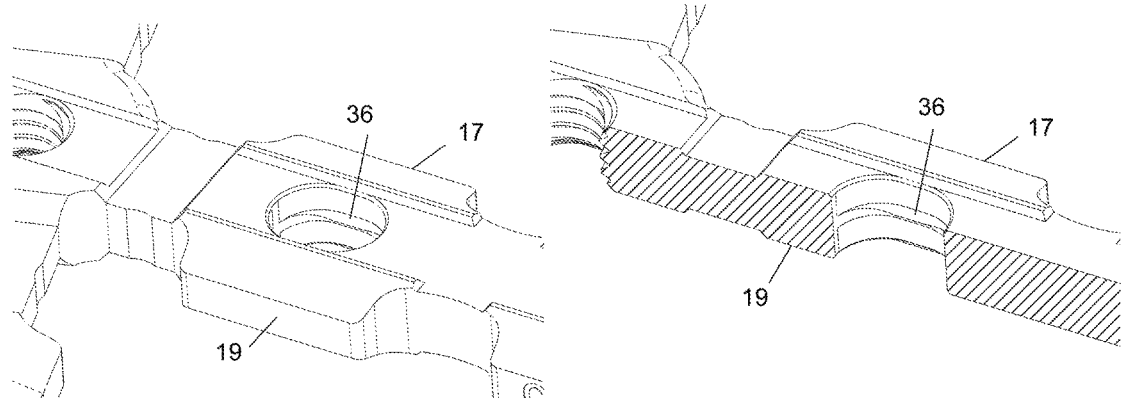
FIG. 22A is an enlarged perspective view of an elongate slot in the plate.
FIG. 22B is a view similar to FIG. 22A shown in longitudinal section.
Figure 23:
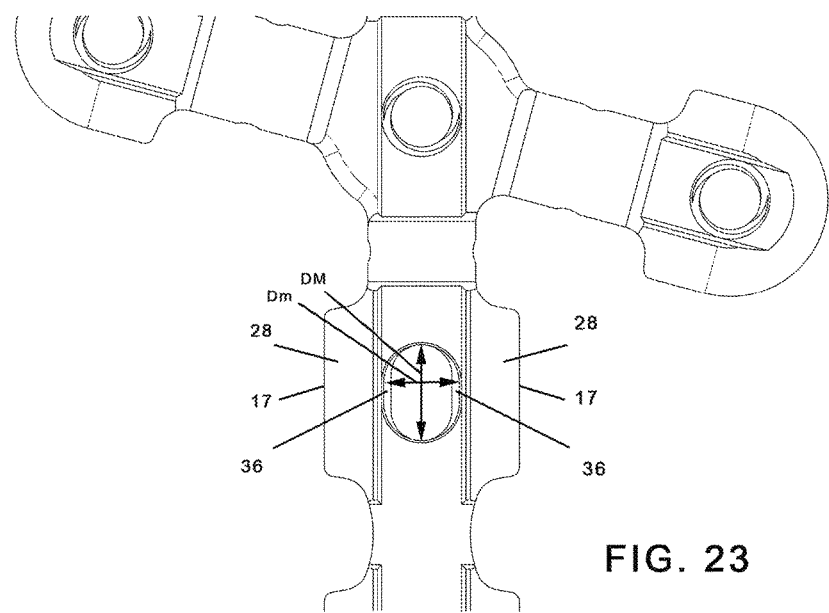
FIG. 23 is an enlarged partial plan view of a portion of the plate containing an elongate slot.

Turning now to FIGS. 22A, 22B and 23, the elongate screw holes or slots 26 have a major diameter $D_M$ and a minor diameter $D_m$. The slots include two thin ledges 36 extending along the long sides of the hole and parallel to the major diameter $D_M$. The ledges 36 have a thickness in the dimension extending between the first and second sides 16, 18, and parallel to the lateral sides 17, 19, of the plate. The ledges 36 taper toward the longitudinal axis of the plate at an angle. The ledges have a width in the lateral dimension. The ledges 36 are located recessed relative to each of the first and second sides 16, 18 of the plate, and more particularly located centrally between the first and second sides. As stated above, the wings 28 taper at a first angle.

Figure 24:
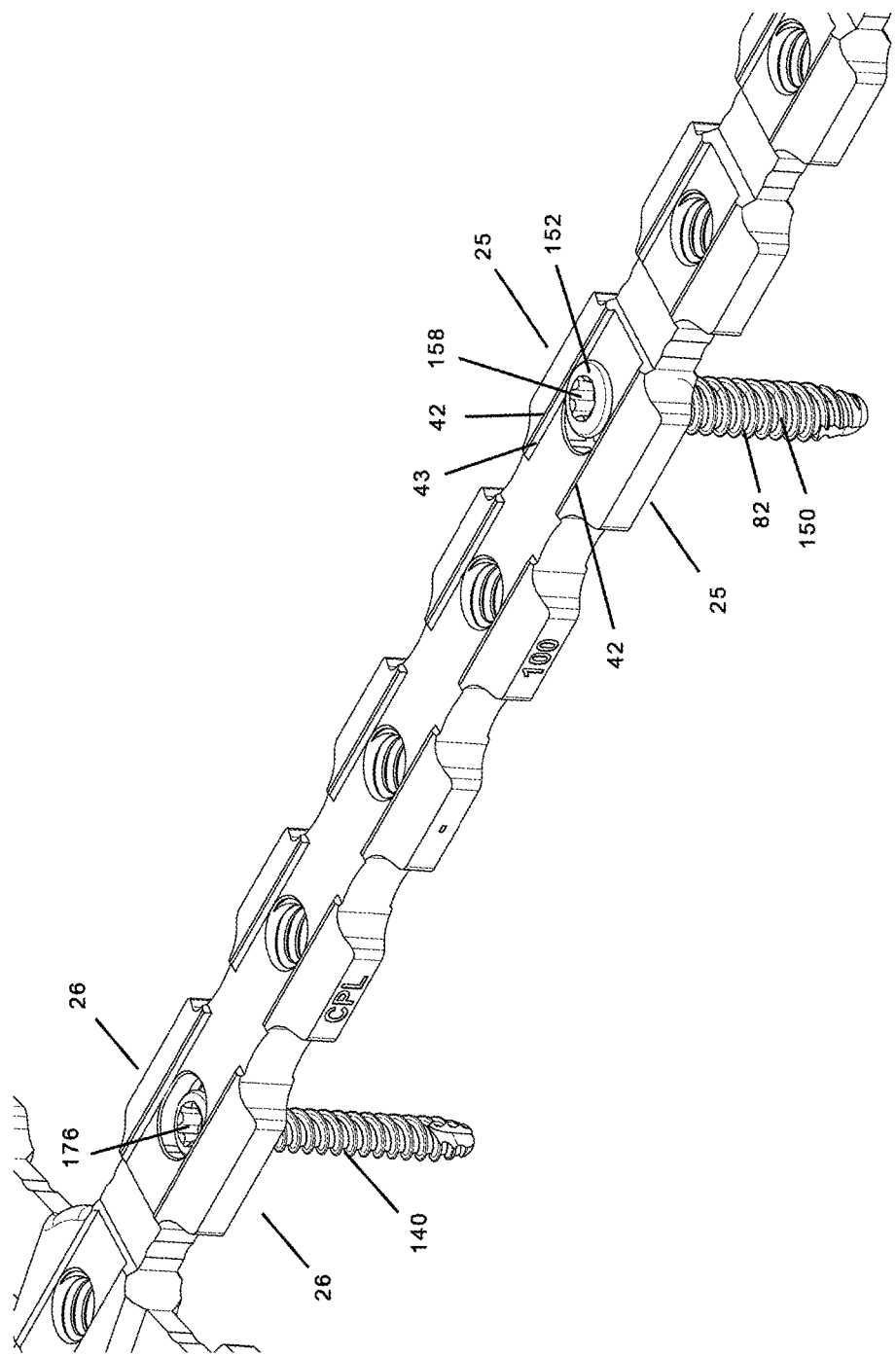
FIG. 24 is a partial perspective view of the bone plate showing a first elongate slot provided with a compression screw and a second elongate slot provided with a locking screw.
Figure 25:
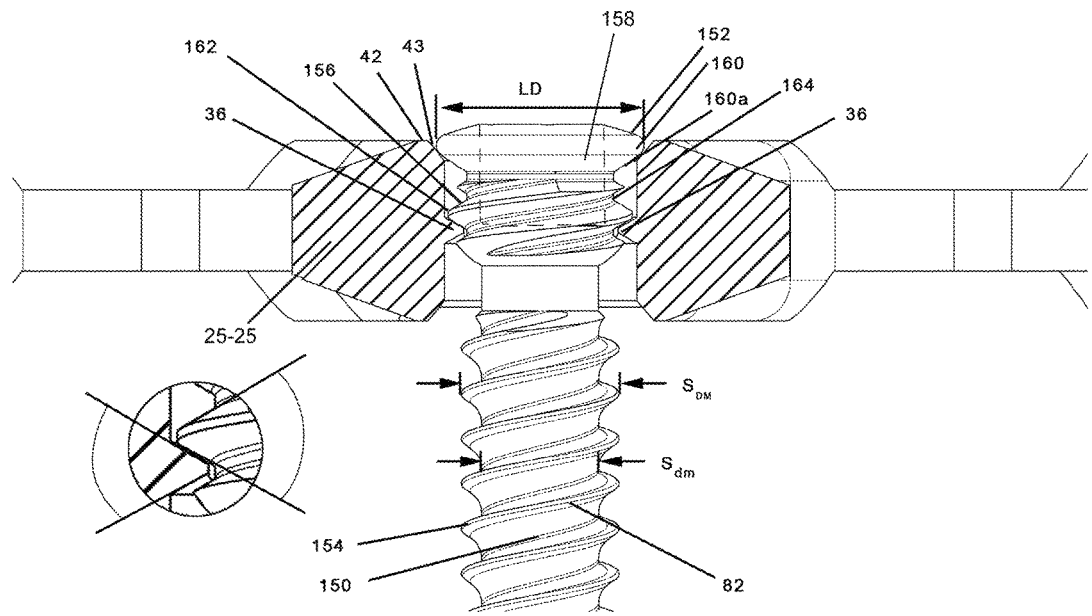
FIG. 25 is a cross-section across line 25-25 in FIG. 24.

Referring to FIGS. 24 and 25, the locking screws 82 each have a shaft 150 and a head 152. The shaft 150 includes bone-engaging threads 154 having a major diameter $S_{DM}$ and a minor diameter $S_{dm}$. The head 152 includes external threads 156, a driver slot 158 for receiving a driver, and an upper lip 160. The threads 156 define a first threaded pitch, a crest 162 (defining a major diameter $H_{DM}$), a root 164 (defining a minor diameter $H_{dm}$), and a thread angle between the crest 162 and the root 164. The thickness of the ledge 36 is less than the first thread pitch. The angle of taper of the ledge 36 is preferably substantially the same (±5°) as the thread angle between the crest 162 and root 164. The width of the ledge 36 is preferably approximate to, or slightly smaller than, the difference between the crest and root dimensions, or (major diameter−minor diameter)/2. The lip 160 has a diameter $L_D$ greater than the minor diameter $D_m$ of the elongate slot 26 (FIG. 23). The lower surface 160*a* of the lip 160 optionally extends at substantially a same angle (±5°) as the medial surfaces 43 of the rails 42. When the locking screw 82 is driven into the elongate slot 26, the ledge 36 functions as a single thread, and the threads on the head 156 threadedly engage the ledge. As such, the locking screw 82 is threadedly advanced into the plate relative to the ledge, and locked relative thereto. Also, the locking screw 82 can be advanced only until the lower surface of the lip 160 stops against the beveled medial surface 43 of the rail 42 laterally surrounding the slot, which forms a seat for the locking screw.

Figure 26:
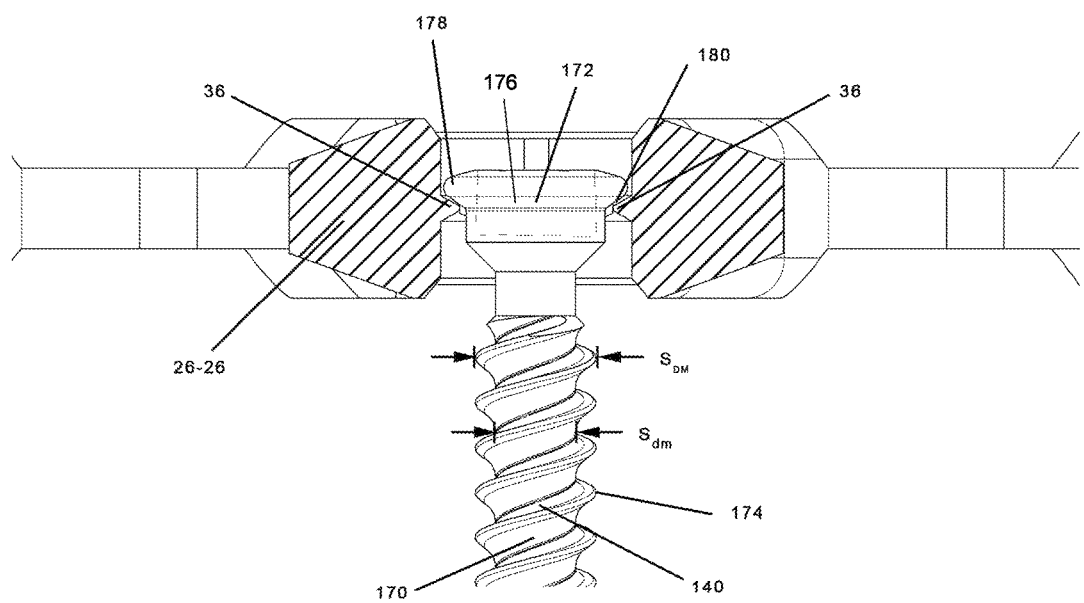
FIG. 26 is a cross-section across line 26-26 in FIG. 24.

Referring to FIGS. 24 and 26, the compression screws 140 each have a shaft 170 and a head 172. The shaft 170 includes bone-engaging threads 174 having a major diameter $S_{DM}$ and a minor diameter $S_{dm}$. The head 172 includes a driver slot 176 for receiving a rotational driver and an upper lip 178 that is smaller than a minor diameter of the slot 26 adjacent to, but not between, the ledges 36. The lower surface 180 of the lip 178 extends at an angle that preferably approximates the facing surface of the ledge 36. When the compression screw 140 is driven into the elongate slot 26, the ledge 36 functions as a stop which the lip 178 contacts in applying compression to the plate.

Figure 27:
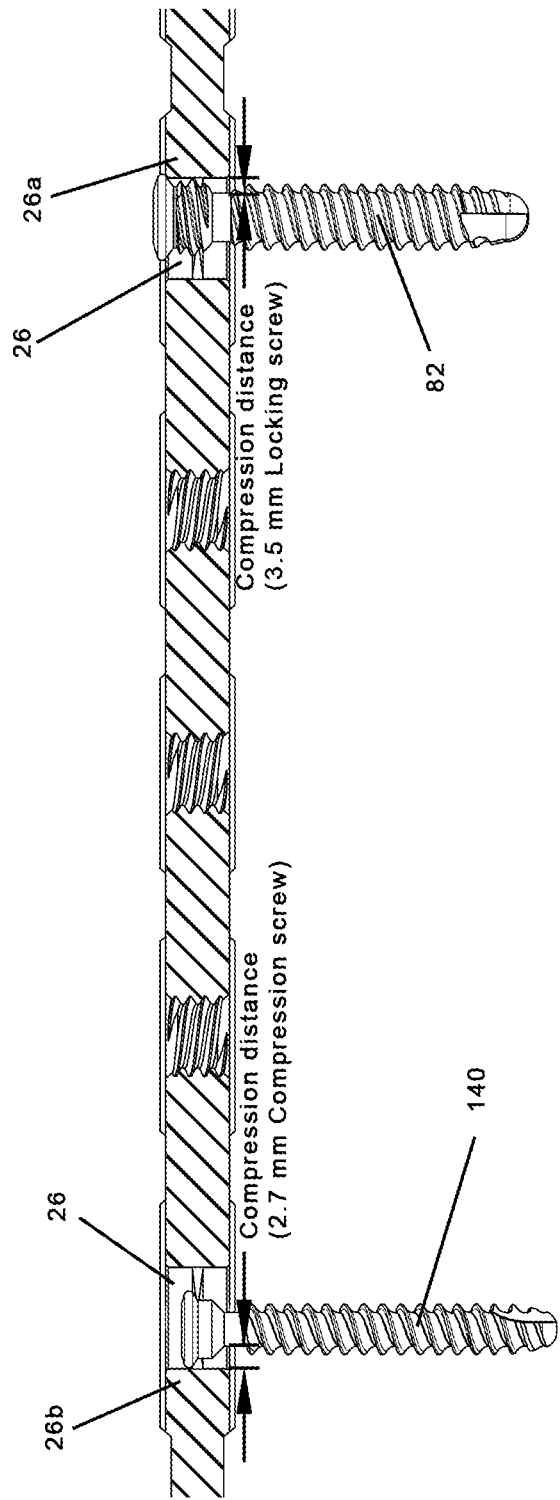
FIG. 27 is a longitudinal section view across the bone plate and screws shown in FIG. 24.

In addition, referring to FIGS. 24 and 27, each of the locking screw 82 and compression screw 140 are adapted to provide dynamic compression; i.e., longitudinal displacement across a fracture, as the respective screw is driven into a respective elongate slot 26. That is, when the screw is inserted at one end of the elongate slot, the head of the respective screw imparts a horizontal force component when driven vertically into contact against the plate. By way of example, locking screw 82 is inserted adjacent the end 26*a* of the slot in which displacement of the plate is intended. As the screw 82 is advanced toward a locking configuration with the plate, the head displaces the plate by up to a distance corresponding to (major diameter of the head thread−minor diameter of the shaft thread)/2. In one locking screw with a 3.5 mm shaft major diameter, the longitudinal displacement is (4.1 mm−2.6 mm)/2=0.75 mm. To effect dynamic compression with the compression screw 140, the screw is also inserted adjacent an end 26*b* of the slot in which displacement of the plate is intended. As the screw is advanced into compression against the plate, the head displaces the plate by up to a distance corresponding to (diameter of the lip at the head−minor diameter of the shaft thread)/2. In one compression screw with a 2.7 mm shaft major diameter, the longitudinal displacement is (4.1 mm−2.1 mm)/2=1.0 mm. As such, in the described set of locking screw and compression screw, the locking screw effects 75% of the longitudinal compression of the compression screw; this result is at the median of a preferred relationship (75%±15%, or 60%-90%) of the relative longitudinal, or dynamic, compression between the two types of screws.

The system provides a single plate design that accommodates left and right anatomies and which can also be customized in shape via removal of one or more nodes and bending along one or more bridges. The single plate design is readily adaptable into treatment even for those surgeons who have not had significant prior experience with anatomical or shapeable plates adapted for specific bones.

There have been described and illustrated herein several embodiments of a bone plate system including bone plates, plate benders, and screws, and methods of implanting the plate in bones of a mammal. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A bone plate for fixation of a bone, comprising:
a body portion having a first side and an opposite second side, the body portion extending in a plane,
the bone plate including a plurality of nodes and intervening bridges, the bridges having a reduced area moment of inertia relative to the nodes such that the bridges have an increased propensity to bending relative to the nodes when a force is applied thereto, and each of the nodes having a screw hole, wherein at least a plurality of the screw holes are threaded,
wherein the nodes and bridges present a same surface structure when viewed from either of the first and second sides such that both of the first and second sides are reversibly configured for placement onto the bone.

2. The bone plate of claim 1, wherein:
the body portion is straight.

3. The bone plate of claim 1, further comprising:
a cross-arm extending transverse to the body portion.

4. The bone plate of claim 3, wherein:
the cross-arm extends at a non-orthogonal angle relative to the body portion.
5. The bone plate of claim 3, wherein:
the body portion and cross-arm together define a t-shape.
6. The bone plate of claim 1, wherein:
the plate is bilaterally asymmetric.
7. The bone plate of claim 1, wherein:
each of the first and second sides have exactly the same surface structure.
8. The bone plate of claim 1, wherein:
the first and second sides at the nodes are provided with a longitudinal channel.
9. The bone plate of claim 1, wherein:
the screw holes include a countersink at each of the first and second sides.
10. The bone plate of claim 8, wherein:
the nodes include rails extending longitudinally along the channel.
11. The bone plate of claim 1, wherein:
the nodes have bilaterally extending wings that laterally taper in thickness.
12. The bone plate of claim 11, wherein:
the wings equally taper relative to the first and second sides of the plate.
13. A bone plate for fixation of a bone, consisting of:
a body portion having a first side and an opposite second side, the first and second sides having a common structure such that the body portion is reversible for placement onto the bone, and
a cross-arm extending transverse to the body portion at a non-orthogonal angle,
the bone plate including a plurality of alternating nodes and bridges, the bridges having a reduced area moment of inertia relative to the nodes such that the bridges have an increased propensity to bending relative to the nodes when a force is applied thereto, at least a plurality of the nodes having a screw hole, and at least a plurality of the screw holes are threaded and include a countersink at each of the first and second sides,
the extension of the nodes and bridges defining a first axis extending along the straight body portion, and second axis extending along the cross-arm,
the nodes including a recessed channel at each of the first and second sides, the each recessed channel extending longitudinally along the respective first and second axes, and the nodes having bilateral wings laterally taper in thickness.
14. The bone plate of claim 13, wherein:
the body portion and cross-arm together define a t-shape.
15. The bone plate of claim 13, wherein:
the plate is bilaterally asymmetric.
16. A system for fixation of a bone, comprising:
a) a first bone plate including a body portion having a first side and an opposite second side, and lateral sides extending between the first and second sides,
the first bone plate including a plurality of nodes and intervening bridges, the bridges having a reduced area moment of inertia relative to the nodes such that the bridges have an increased propensity to bending relative to the nodes when a force is applied thereto, and each of the nodes having a screw hole,
wherein at least a plurality of the screw holes are threaded and include a countersink at each of the first and second sides,
wherein the nodes and bridges are the same at each of the first and second sides; and
b) a set of screws, including
a plurality of locking screws having a threaded head for threadedly engaging the threaded screw holes and a threaded shaft, and
at least one compression screw having a compression head and a threaded shaft, the compression head adapted to apply a compressive force against the first bone plate when the threaded shaft engages the bone and clamps the first bone plate between the compression head and the bone.
17. The system of claim 16, wherein:
the nodes define recessed channels at each of the first and second sides, the channels at each of the first and second sides of the plate have a pair of rails, and
the threaded screw hole of a node is located between the pair of rails at each of the first and second sides.
18. The system of claim 16, further comprising:
a second bone plate; and
a third bone plate,
wherein the first, second and third bone plates have a common shape with each other, and the first, second and third bone plates have a different size relative to each other, and
wherein the set of screws is adapted to also engage screw holes in each of the second and third bone plates.
19. The system of claim 16, further comprising:
first and second plate bending tools for shaping the first bone plate, at least one of the bending tool including,
a bracket having arms including seats at the end thereof, a space defined between the arms, wherein when the first side of the first bone plate is in contact with bone and the second side of the first bone plate is face up, the arms are adapted to surround the lateral sides of the first bone plate and the seats are adapted to extend under the first side of the first bone plate; and
a handle movable relative to the bracket to contact the second side of the first bone plate and clamp the first bone plate between a portion of the handle and the seats of the bracket.
20. The system of claim 19, wherein:
when the second side of the first bone plate is in contact with bone and the first side of the first bone plate is face up, the arms are adapted to surround the lateral sides of the first bone plate and the seats are adapted to extend under the second side of the first bone plate, and when the handle is moved relative to the bracket a portion of the handle clamps the first bone plate between the portion of the handle and the seats of the bracket.
21. The system of claim 19, wherein:
the portion of the handle is a bolt at a distal end of the handle, rotation of the handle moves the bolt between opened and closed position, and in the closed position the bolt extends at least partially into a screw hole of a node, the screw hole has an axis, and the bolt extends at an angle relative to the axis in the closed position.
22. A system for fixation of a bone, comprising:
a) a bone plate including a body portion having a first side and an opposite second side, and lateral sides extending between the first and second sides,
the bone plate including at least one elongate screw slot having a major diameter, a minor diameter, parallel rails at each of the first and second sides that protrude relative to the elongate screw slot, the rails each including a medial surface beveled at an angle, and a pair of ledges extending parallel to the major diameter, the ledges recessed and equally displaced relative to each of the first and second sides, the ledges having a thickness in a dimension extending between the first and second sides of the bone plate;

b) a locking screw including a shaft and a head, the head including an upper lip and external threads, the upper lip having a diameter greater than the minor diameter of the elongate slot, and the upper lip having a lower surface that extends at an angle, the external threads defining a crest, a root, and a thread pitch, wherein the thread pitch is greater than the thickness of the ledge so that the locking screw threadedly engaged relative to the ledge, and the shaft defining a screw axis, wherein the locking screw can be advanced into the elongate slot until the lower surface of the upper lip stops against the rails.

23. The system according to claim 22, wherein:
the crest and the root of the external threads on the head define a thread angle, the ledge between the first and second sides has an angle of taper toward the major diameter of the screw slot, and the angle of taper is substantially the same as the thread angle.

24. The system according to claim 22, wherein:
the thickness of the ledge is less than first thread pitch.

25. The system according to claim 22, wherein:
a width of the ledge approximates a difference between the crest and root dimensions.

26. The system according to claim 22, wherein:
the angle of the lower surface of the lip and the angle of the medial surface of the rails are the same relative to the screw axis.

27. The system according to claim 22, further comprising:
at least one compression screw having a head and a threaded shaft, the head having a diameter small than the minor diameter of the screw slot and sized to seat against the ledges to apply a compressive force against the first bone plate.

28. The system according to claim 27, wherein:
each of the locking screw and the compression screw are adapted to impart horizontal displacement of the bone plate when inserted at one end of the elongate slot such that the head of the screw imparts a horizontal force component when driven vertically into contact against the plate.

29. The system according to claim 27, wherein:
the bone plate includes a plurality of threaded screw holes, each adapted to receive either of the locking screw and the compression screw.

30. The system according to claim 27, wherein:
the bone plate including a plurality of nodes and intervening bridges, the bridges having a reduced area moment of inertia relative to the nodes such that the bridges have an increased propensity to bending relative to the nodes when a force is applied thereto, and each of the nodes having a screw hole,
wherein the nodes and bridges present a same surface structure when viewed from either of the first and second sides.

31. The system according to claim 30, wherein:
at least a plurality of the screw holes are threaded and include a countersink at each of the first and second sides.

32. A system for fixation of a bone, comprising:
a) a bone plate including a body portion having a first side and an opposite second side, and lateral sides extending between the first and second sides, the first and second sides having a common structure such that the plate is reversible for placement onto the bone,
the bone plate including at least one elongate screw slot having a major diameter, a minor diameter, and a pair of ledges extending parallel to the major diameter, the ledges recessed and equally displaced relative to each of the first and second sides, the ledges having a thickness in a dimension extending between the first and second sides of the bone plate;

b) a locking screw, including a shaft and a head, the head including an upper lip and external threads, the external threads defining a crest, a root, and a thread pitch, wherein the thread pitch is greater than the thickness of the ledge so that the locking screw can be threadedly engaged relative to the ledge, and the shaft defining a screw axis.

* * * * *